United States Patent
Yu et al.

(10) Patent No.: US 7,567,838 B2
(45) Date of Patent: Jul. 28, 2009

(54) METHOD FOR SENSING CARDIAC CONTRACTILE FUNCTION USING A LEAD INSERTABLE MOTION SENSOR

(75) Inventors: Nancy Yu, Maplewood, MN (US); Jiang Ding, Maplewood, MN (US); Qingsheng Zhu, Little Canada, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 656 days.

(21) Appl. No.: 11/254,344

(22) Filed: Oct. 20, 2005

(65) Prior Publication Data

US 2006/0041298 A1  Feb. 23, 2006

Related U.S. Application Data

(62) Division of application No. 10/004,686, filed on Dec. 5, 2001, now Pat. No. 6,980,866, and a division of application No. 10/008,397, filed on Dec. 6, 2001, now Pat. No. 6,993,389.

(51) Int. Cl.
*A61N 1/37* (2006.01)

(52) U.S. Cl. ............ 607/9; 607/6; 607/14; 607/17; 600/515; 600/526

(58) Field of Classification Search .......... 607/6, 607/17, 19; 600/587
See application file for complete search history.

(56) References Cited

U.S. PATENT DOCUMENTS

| | | |
|---|---|---|
| 3,787,641 A | 1/1974 | Santori |
| 4,211,951 A | 7/1980 | Jensen |
| 4,574,814 A | 3/1986 | Buffet |
| 5,024,239 A | 6/1991 | Rosenstein |
| 5,194,859 A | 3/1993 | Warren |
| 5,472,453 A | 12/1995 | Alt |
| 5,496,361 A | 3/1996 | Moberg et al. |
| 5,628,777 A | 5/1997 | Moberg et al. |
| 5,899,927 A | 5/1999 | Ecker et al. |
| 6,070,101 A | 5/2000 | Struble et al. |
| 6,077,236 A | 6/2000 | Cunningham |

(Continued)

FOREIGN PATENT DOCUMENTS

EP  515319 A2  12/1992

(Continued)

OTHER PUBLICATIONS

U.S. Appl. No. 10/004,686, filed Dec. 5, 2001, Prosecution History, 45 pgs.

*Primary Examiner*—Kennedy J Schaetzle
(74) *Attorney, Agent, or Firm*—Schwegman, Lundberg & Woessner, P.A.

(57) ABSTRACT

Systems and methods for detecting and measuring cardiac contractile function of a heart using an acceleration sensor unit inserted within the heart, such as within a vein of the cardiac wall are disclosed. The systems and methods involve detecting the occurrence of electrical events within the patient's heart by inserting and positioning an implantable lead having an electrode near a cardiac wall as well as detecting mechanical events within the patient's heart by then inserting and positioning a cardiac motion sensor unit through the inner lumen of the implantable lead. Furthermore, the systems and methods do not require dedicated leads and may be used with preexisting implantable leads.

21 Claims, 3 Drawing Sheets

U.S. PATENT DOCUMENTS

| | | |
|---|---|---|
| 6,243,603 B1 | 6/2001 | Ideker et al. |
| 6,711,443 B2 | 3/2004 | Osypka |
| 7,181,268 B2 * | 2/2007 | Sheldon et al. ............. 600/513 |
| 2002/0077568 A1 | 6/2002 | Haddock |

FOREIGN PATENT DOCUMENTS

| | | |
|---|---|---|
| WO | WO95/33517 | 6/1994 |
| WO | WO-95/33517 A1 | 12/1995 |

* cited by examiner

METHOD FOR SENSING CARDIAC CONTRACTILE FUNCTION USING A LEAD INSERTABLE MOTION SENSOR

CROSS REFERENCE TO RELATED APPLICATIONS

This application is a divisional of U.S. patent application Ser. No. 10/004,686, filed Dec. 5, 2001, now issued as U.S. Pat. No. 6,980,866, and is a divisional of U.S. patent application Ser. No. 10/008,397, file Dec. 6, 2001, now issued as U.S. Pat. No. 6,993,389, said application incorporated herein by reference.

TECHNICAL FIELD

The present invention relates to cardiac sensing devices. More specifically, the present invention relates to insertable acceleration sensor units that provide signals representative of cardiac mechanical activity.

BACKGROUND

Implantable cardiac sensing and stimulating devices are generally used to manage a variety of heart arrhythmias and conduction system blockages. Heart arrhythmias, such as bradycardia and tachycardia, often prevent the heart from pumping an adequate amount of blood. When the body does not receive enough oxygen-carrying blood, symptoms such as fatigue, shortness of breath, dizziness, and unconsciousness may occur. Furthermore, conduction system blockages in the heart cause slow, asynchronous contractions that reduce the pumping efficiency and lower cardiac output. Implantable cardiac sensing and stimulating devices must be capable of detecting such arrhythmias and decreased pumping efficiency due to conduction system blockages, and the implantable device should respond to the detected arrhythmia or low pumping efficiency by providing therapeutic electrical stimulation.

Accurate measurement of cardiac activity is needed to deliver effective therapy by an implantable cardiac sensing and stimulating device. Many cardiac sensing and stimulating devices that detect and distinguish among cardiac arrhythmias monitor heart rate, which is usually accomplished by measuring cardiac electrical activity. Furthermore, the functions of the conduction system and synchronization of cardiac wall contractions are assessed by measuring and analyzing cardiac electrical activity. However, electrical activity is not a sufficiently accurate representation of the mechanical function of the heart. Thus, using only electrodes to sense cardiac mechanical activity can have some disadvantages in some circumstances.

Some implantable cardiac sensing and stimulating devices include implantable leads with built-in accelerometers to measure cardiac mechanical movement representative of cardiac contractile function. However, built-in accelerometers typically require a dedicated implantable lead, which tends to be bulky and hard to handle. Furthermore, these conventional leads with built-in accelerometers are too large to fit within a vein of a cardiac wall and require invasive installation procedures.

Thus, it is desirable to provide an improved sensing method and system for accurately detecting and monitoring cardiac mechanical activities. Further, it is desirable to provide an improved sensing method and system that has the ability to be implanted without a dedicated lead, such as within a preexisting implantable lead that may be positioned within a vein of a cardiac wall.

SUMMARY

As embodied and broadly described herein, the present invention relates to a method for detecting and measuring cardiac contractile functions using a signal representative of cardiac wall acceleration provided by an acceleration sensor unit. The method involves introducing the acceleration sensor unit into a vein of the cardiac wall and positioning the sensor so that it responds to the acceleration of the cardiac wall and provides a signal representative of the cardiac wall acceleration. The method further involves connecting the acceleration sensor unit to an electronic device.

Moreover, the present invention also relates to another method for detecting and measuring cardiac contractile functions using a signal representative of cardiac wall acceleration provided by an acceleration sensor. This method involves inserting a guide element along the inner lumen of an implantable lead. The method also involves introducing the implantable lead into a vein of the cardiac wall. The method further involves positioning the implantable lead within the vein using the guide element and then removing the guide element from the inner lumen of the implantable lead. Finally, the method involves inserting the acceleration sensor unit along the inner lumen of the implantable lead.

In another embodiment, the present invention relates to a method for creating an acceleration sensor. This method involves providing an implantable lead and inserting a cardiac motion sensor along the inner lumen of the implantable lead. This method also involves positioning the cardiac motion sensor within the lumen of the implantable lead so that the cardiac motion sensor remains mobile along the longitudinal axis of the implantable lead.

Further, the present invention also relates to a system for detecting and measuring cardiac contractile functions. This system includes an acceleration sensing means disposed at the cardiac wall for providing a signal representative of acceleration of the cardiac wall. This system also includes a conductor means molded into an elongated insulator body for transmitting a signal representative of acceleration of the cardiac wall from the acceleration sensing means to the electronic sensing means. This system further includes a connector means for electrically linking the conductor means to the electronic sensing means.

The present invention also relates to another system for detecting and measuring cardiac contractile functions. This system includes an acceleration sensing device disposed at the cardiac wall for providing a signal representative of acceleration of the cardiac wall. The system also includes a conductor device molded into an insulated elongate body for transmitting a signal representative of acceleration of the cardiac wall from the acceleration sensing device to the electronic device. This system further includes a connector device for electrically linking the conductor device to the electronic device.

Advantages of the invention will be set forth in part in the description which follows or may be learned by practice of the invention. It is to be understood that both the foregoing general description and the following detailed description are exemplary and explanatory only and are not restrictive of the invention, as claimed.

DETAILED DESCRIPTION

Figure 1:
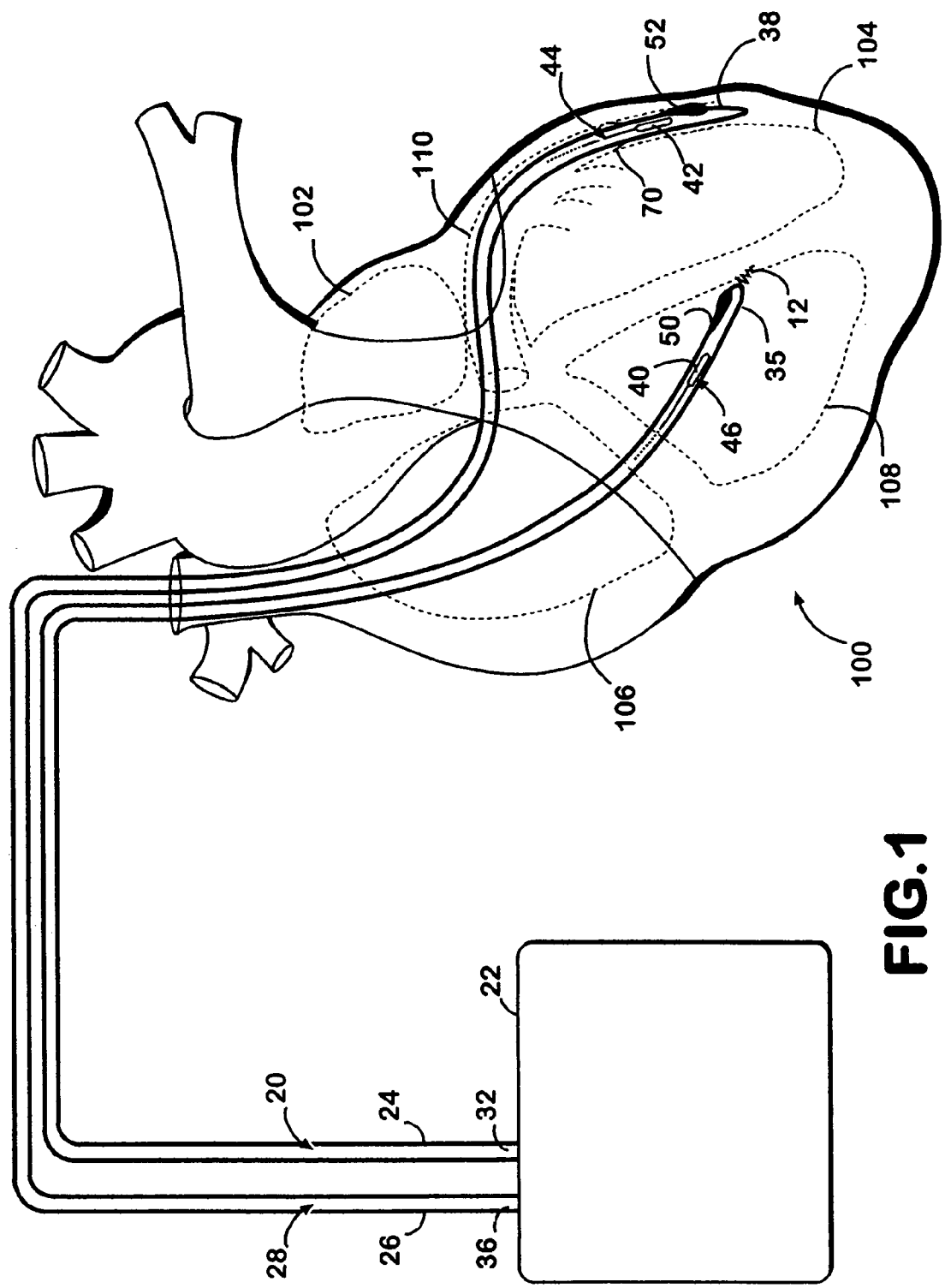
FIG. 1 is a schematic representation of a typical human heart with acceleration sensor units in accordance with embodiments of the present invention.

Various embodiments of the present invention will be described in detail with reference to the drawings, wherein like reference numerals represent like parts and assemblies through the several views. Reference to various embodiments does not limit the scope of the invention, which is limited only by the scope of the claims attached hereto.

Embodiments of the present invention allow detection and measurement of cardiac contractile functions by an acceleration sensor unit inserted within the heart, such as within a vein of the cardiac wall. These embodiments also provide systems and methods that may be used without requiring a dedicated lead for the acceleration sensor. Further, these embodiments provide systems and methods that may be used with preexisting leads. Certain of these embodiments also provide systems and methods that may be removed from implantable leads without disturbing the position of the implantable lead within the heart 100.

FIG. 1 is a schematic representation of a typical human heart with acceleration sensor units in accordance with embodiments of the present invention. In FIG. 1, the heart 100 comprises the upper heart chambers, the right atrium area 106 and left atrium area 102, and the lower heart chambers, the right ventricle area 108 and left ventricle area 104. The coronary sinus 110 extends from the opening in the right atrium 106 laterally around the atria to form the great cardiac vein that extends further inferiorly into branches of the great cardiac vein. An electronic device 22 having leads 24, 26 is implanted in a human body (not shown) with portions of the implantable leads 24 and 26 inserted into the heart 100 and/or veins of the heart 100. The device 22 is used to detect and analyze electrical cardiac signals and signals indicative of cardiac wall acceleration produced by the heart 100 and to provide electrical energy to the heart 100 under certain predetermined conditions to treat arrhythmias or conduction system blockages. As shown, the electronic device 22 may be an implantable cardiac resynchronization device for establishing synchronization of ventricular wall contractions, such as for patients with a left bundle branch blockage.

The implantable leads 24 and 26 comprise elongate bodies, both having a proximal end, 32 and 36 respectively, and a distal end, 35 and 38 respectively. The implantable leads 24 and 26 further include one or more pacing/sensing electrodes 50, 52 respectively and/or one or more acceleration sensor units 46, 44. The implantable lead 26 is passed through a vein into the right atrium chamber 106 of the heart 100, into the coronary sinus 110 and then inferiorly in the great cardiac vein in a basal region to extend the electrode 52 located at the distal end 38 onto the cardiac wall alongside the left atrium chamber 102 of the heart 100. In an alternative embodiment, the implantable lead 26 may be extended further into the coronary sinus 110 and anterior and/or lateral veins extending therefrom to extend the electrode 52 located at the distal end 38 onto the cardiac wall alongside the left ventricle chamber 104 of the heart 100. In one embodiment, the implantable lead 26 is fixed in place by a distal fixation mechanism 70 comprising a plurality of fixation tines well known in the art.

When the implantable lead 26 is positioned within the coronary sinus 110, an acceleration sensor unit 44 is passed through the inner lumen 28 of the implantable lead 26 to extend the cardiac motion sensor 42, such as an accelerometer, of the acceleration sensor unit 44 alongside preferably either the left ventricle chamber 104 or left atrium chamber 102 of the heart 100. The acceleration sensor unit 44 may be removed from the inner lumen 28 of the implantable lead 26 without removing the implantable lead 26 from the coronary sinus 110 of the heart 100.

In an additional embodiment, the implantable lead 24 is passed into the right atrium chamber 106 of the heart 100 and through the tricuspid valve into the right ventricle 108 where the electrode 50, located at the distal end 35, is fixed in place in the interventricular septum by a distal attachment mechanism 62. The distal attachment mechanism 62 may be a wire shaped into a helical cork-screw like projection, a plurality of fixation tines projecting away from the peripheral surface of the implantable lead 24, or other structures for attaching the lead 24. Such distal attachment mechanisms are well known in the art and are intended to embed the distal end of the lead 24 in the tissue of the heart. When the implantable lead 24 is fixed in place, an acceleration sensor unit 46 is passed through the inner lumen 20 of the implantable lead 24 to extend the cardiac motion sensor 40 located at the distal end of the acceleration sensor unit 46 to the interventricular septum. The acceleration sensor unit 46 may be later removed from the inner lumen 20 of the implantable lead 24, if necessary, without removing the implantable lead 24 from the interventricular septum of the heart 100.

The implantable device 22 may detect electrical events as well as mechanical events within the heart 100. The electrodes 50, 52 placed into the heart 100, including the electrode in the coronary sinus vein branch 110, sense the naturally occurring depolarization of the cells as the electrical wave travels past the electrode 50, 52 down the surface of the heart 100 from the atrium area to the ventricle area. The acceleration sensor units 44, 46 inserted through the inner lumens 20, 28 of the implantable leads 24, 26 sense the cardiac contractile functions by providing a signal indicative of cardiac wall acceleration.

The illustrated types and locations of implantable leads 24, 26, electrodes 50, 52 and acceleration sensor units 44, 46 are merely exemplary. It will be understood that one or more other types of endocardial and epicardial leads, electrodes and acceleration sensor units located in or about the right and left chambers of the heart 100 as well as the coronary sinus 110 can be substituted for those illustrated in FIG. 1 described above.

Figure 2:
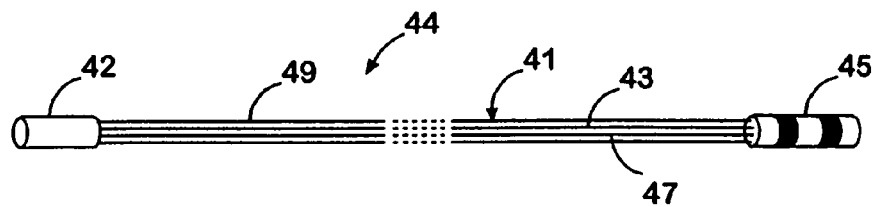
FIG. 2 depicts an acceleration sensor unit in accordance with an embodiment of the present invention.

FIG. 2 illustrates an example of an acceleration sensor unit in accordance with the present invention. In FIG. 2, the acceleration sensor unit 44 comprises a cardiac motion sensor 42 and a connector 45 coupled together by an elongate body 41. The elongate body 41 comprises two electrical conductors 43, 47 encompassed by an insulator 49 extending longitudinally. The electrical conductors 43, 47 electrically connect the cardiac motion sensor 42 located at the distal end of the acceleration sensor unit 44 with the connector 45 located at the proximal end of the acceleration sensor unit 44. In one embodiment, the insulator 49 of the elongate body 41 is an implantable polyurethane, silicone rubber or other implantable flexible polymer. At the distal end of the acceleration sensor unit 44, the electrical conductors 43, 47 connect with the cardiac motion sensor 42. At the proximal end of the acceleration sensor unit 44, the electrical conductors 43, 47 connect with the connector 45. Standard electrical bipolar or unipolar connectors may be used as the connector 45, which provides mechanical and electrical connections to the electronic device 22. The electrical conductors 43, 47 transmit the signal indicative of cardiac wall motion from the cardiac motion sensor 42 to the electronic device 22.

In accordance with the present invention, a preferred embodiment of the cardiac motion sensor 42 is constructed as an accelerometer that is particularly sized for incorporation within a vein of a cardiac wall of the heart 100. In another embodiment, the cardiac motion sensor 42 is constructed as an accelerometer that is particularly sized for incorporation in an implantable lead within a vein of a cardiac wall of the heart 100. Suitable accelerometers include, for example, the miniaturized accelerometer provided by Ball Semiconductor Inc. (see U.S. Pat. No. 6,197,610) and others that has a diameter of approximately 1 millimeter. The cardiac motion sensor 42 can be an accelerometer formed by any available technology such as piezoelectric, piezoresistive, capacitive, inductive, or magnetic. The cardiac motion sensor 42 detects and measures cardiac wall motion and provides a signal representative of cardiac wall acceleration to the electrical conductors 43, 47 which then transmit the signal to the electronic device 22.

Figure 3:
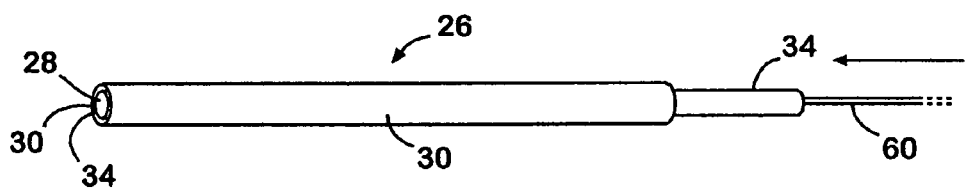
FIG. 3 illustrates an implantable lead incorporating a guide element and an acceleration sensor unit in accordance with an embodiment of the present invention.
Figure 3:
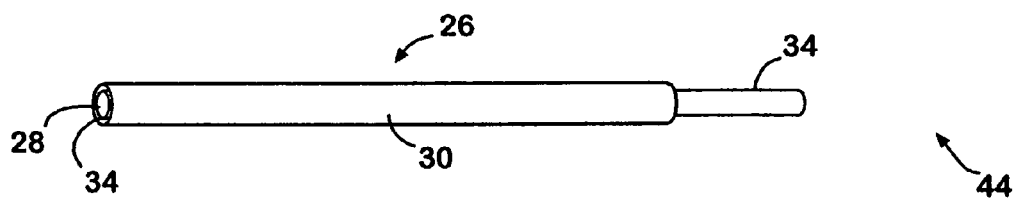
Figure 3:
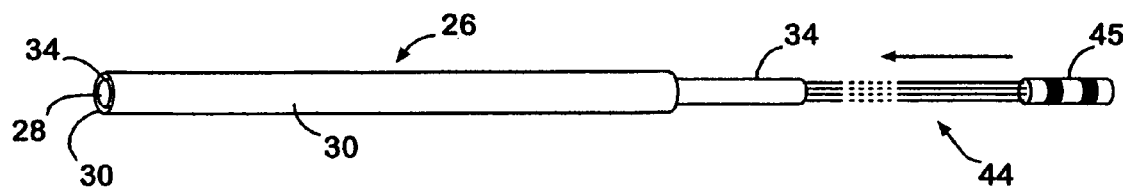

FIG. 3 illustrates an implantable lead 26 incorporating a guide element 60 and an acceleration sensor unit 44 in accordance with the present invention. The implantable lead 26 comprises a cylindrical lead 34 with a conductor used for sensing cardiac electrical activity and delivering stimulation to the cardiac wall. The cylindrical lead 34 is concentrically encompassed by a second cylindrical lead 30 possessing a similar conductor, and the cylindrical lead 34 has an inner lumen 28. The conductor of the cylindrical lead 34 and second cylindrical lead 30 may be an electrically conductive metal, as known in the art, formed into an insulated coil configuration such as the Guidant EASYTRAK lead, or in other configurations such as a woven conductor. Moreover, the cylindrical lead 34 and second cylindrical lead 30 may have tapered distal ends.

The implantable lead 26 is adapted to receive a guide element 60 along the inner lumen 28 of the implantable lead 26 for stiffening and shaping the implantable lead 26 during the insertion of the implantable lead 26 into the heart 100. Preferable guide elements include, for example, standard percutaneous transluminal coronary angioplasty guide wires. Once the guide element 60 is used to position the implantable lead 26 within the heart 100 or veins of the heart 100, the guide element 60 is removed from the inner lumen 28 of the implantable lead 26.

In an embodiment of the present invention, acceleration sensor unit 44 is passed through the inner lumen 28 extending along the longitudinal axis of the implantable lead 26 after the implantable lead 26 is positioned within the heart 100, such as within the coronary sinus 110. The acceleration sensor unit 44 is extended into the implantable lead 26 to optimally position the cardiac motion sensor 42 of the acceleration sensor unit 44. For example, the sensor 42 may be positioned adjacent to the left atrium chamber 102 or left ventricle chamber 104 of the heart 100. Once an optimal position for the cardiac motion sensor 42 is achieved, the acceleration sensor unit 44 is fixed relative to the longitudinal axis of the inner lumen 28 of the implantable lead 26 by connecting connector 45 to the electronic device 22. In this embodiment, the connector 45 may be disconnected from the electronic device 22, and the acceleration sensor unit 44 may be removed from the inner lumen 28 of the implantable lead 26 without removing the implantable lead 26 from the heart 100.

Figure 4:
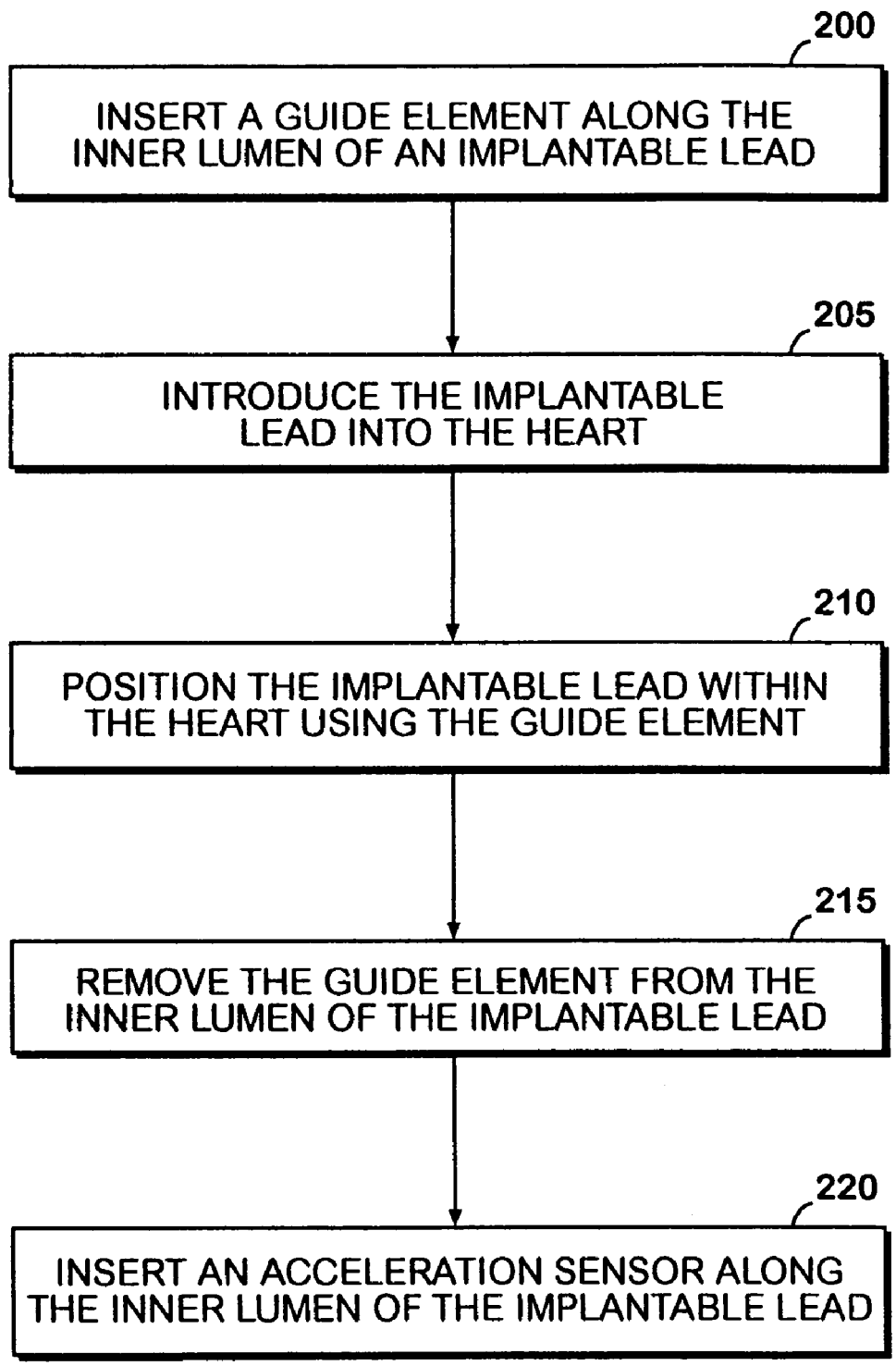
FIG. 4 is a flow chart representing an exemplary method into which an embodiment of the present invention may be incorporated.

FIG. 4 illustrates the steps representing a method into which the present invention may be incorporated. At Step 200, a guide element 60 is inserted along the inner lumen 28 of an implantable lead 26. At Step 205, the implantable lead 26 is introduced into the heart 100, such as within the coronary sinus vein 110 of a cardiac wall. At Step 210, the implantable lead 26 is positioned within the heart 100, such as within the coronary sinus vein 110, using the guide element 60. At Step 215, once the implantable lead 26 has been sufficiently positioned within the heart 100, the guide element 60 is removed from the inner lumen 28 of the implantable lead 26. At Step 220, the acceleration sensor unit 46 is inserted along the inner lumen 28 of the implantable lead 26. Subsequently, should it be necessary, the acceleration sensor unit 46 may be removed from the lead 26 while the lead 26 remains installed in the heart 100.

While the invention has been particularly shown and described with reference to preferred embodiments thereof, it will be understood by those skilled in the art that various other changes in the form and details may be made therein without departing from the spirit and scope of the invention.

What is claimed is:

1. A method of detecting and measuring cardiac contractile functions using a signal representative of cardiac wall movement provided by an acceleration sensor, said method comprising the steps of:

introducing said acceleration sensor unit into a vein of a cardiac wall, wherein the step of introducing said acceleration sensor unit into said vein of said cardiac wall comprises the steps of introducing an implantable lead into said vein of said cardiac wall and then inserting said acceleration sensor unit along an inner lumen of said implantable lead;

positioning said acceleration sensor unit in said vein of said cardiac wall in a manner such that said acceleration sensor unit responds to movement of said cardiac wall and provides said signal representative of cardiac wall movement; and connecting said acceleration sensor unit to an electronic device.

2. The method of claim 1, further comprising the step of removing said acceleration sensor from said vein of said cardiac wall.

3. The method of claim 1, wherein said vein of said cardiac wall is the coronary sinus vein.

4. The method of claim 1, wherein said electronic device is an implantable cardiac resynchronization device.

5. The method of claim 1, further comprising the step of removing said acceleration sensor from said vein of said cardiac wall.

6. The method of claim 1, further comprising the step of removing said acceleration sensor from said inner lumen of said implantable lead while a distal portion of said implantable lead is located within said vein of said cardiac wall.

7. A method of detecting and measuring cardiac contractile functions of a heart using a signal representative of cardiac wall movement provided by an acceleration sensor, said method comprising the steps of:

inserting a guide element along an inner lumen of an implantable lead;

introducing said implantable lead into said heart;

positioning said implantable lead within said heart using said guide element;

removing said guide element from said inner lumen of said implantable lead; and subsequent to removing said guide element, inserting said acceleration sensor unit along said inner lumen of said implantable lead.

8. The method of claim 7, further comprising the step of removing said acceleration sensor from said inner lumen of said implantable lead.

9. The method of claim 7, further comprising the step of connecting said implantable lead and said acceleration sensor unit to an electronic device.

10. The method of claim 7, wherein said implantable lead includes one or more electrodes.

11. The method of claim 10, wherein said acceleration sensor unit is disposed adjacent to said electrodes.

12. The method of claim 7, wherein said implantable lead is positioned within a vein of a cardiac wall of said heart.

13. The method of claim 7, wherein said implantable lead is directly attached to a cardiac wall of said heart.

14. A method of creating a sensor for detecting and measuring cardiac contractile function, said method comprising the steps of:
    inserting a cardiac motion sensor along an inner lumen of an implantable lead; and
    positioning said cardiac motion sensor within said inner lumen of said implantable lead such that said cardiac motion sensor remains mobile relative to the longitudinal axis of said implantable lead.

15. The method of claim 14, further comprising the step of removing said cardiac motion sensor from said inner lumen of said implantable lead.

16. The method of claim 14, wherein said cardiac motion sensor comprises an accelerometer.

17. The method of claim 14, wherein prior to inserting said cardiac motion sensor along said inner lumen of said implantable lead, said method further comprises the steps of:
    connecting a conductor to said cardiac motion sensor;
    passing said conductor through said inner lumen of said implantable lead; and
    connecting said conductor to an electrical device such that said conductor fixes said cardiac motion sensor relative to the longitudinal axis of said lead.

18. The method of claim 17, further comprising the step of removing said cardiac motion sensor from said inner lumen of said implantable lead.

19. The method of claim 14, wherein prior to inserting said cardiac motion sensor along said inner lumen of said implantable lead, said method further comprises the steps of:
    inserting a guide element along the inner lumen of said implantable lead;
    introducing said implantable lead into a vein of a cardiac wall;
    positioning said implantable lead within said vein using said guide element; and
    removing said guide element from said inner lumen of said implantable lead.

20. The method of claim 19, further comprising the step of removing said cardiac motion sensor from said inner lumen of said implantable lead.

21. The method of claim 14, wherein prior to inserting said cardiac motion sensor along said inner lumen of said implantable lead, said method further comprising the step of attaching the implantable lead directly to a cardiac wall.

* * * * *

UNITED STATES PATENT AND TRADEMARK OFFICE
CERTIFICATE OF CORRECTION

| | | |
|---|---|---|
| PATENT NO. | : 7,567,838 B2 | Page 1 of 1 |
| APPLICATION NO. | : 11/254344 | |
| DATED | : July 28, 2009 | |
| INVENTOR(S) | : Yinghong Yu et al. | |

It is certified that error appears in the above-identified patent and that said Letters Patent is hereby corrected as shown below:

On the title page, item (75), in "Inventors", in column 1, line 1, delete "Nancy" and insert -- Yinghong --, therefor.

In column 1, line 10, delete "and" and insert -- which --, therefor.

In column 1, line 11, delete "file" and insert -- filed --, therefor.

Signed and Sealed this

Twenty-ninth Day of December, 2009

David J. Kappos
*Director of the United States Patent and Trademark Office*